(12) United States Patent
Zhou et al.

(10) Patent No.: US 8,962,839 B2
(45) Date of Patent: Feb. 24, 2015

(54) CHIRAL SPIRO-PYRIDYLAMIDOPHOSPHINE LIGAND COMPOUND, SYNTHESIS METHOD THEREFOR AND APPLICATION THEREOF

(75) Inventors: Qilin Zhou, Tianjin (CN); Jianhua Xie, Tianjin (CN); Xiaoyan Liu, Tianjin (CN); Jianbo Xie, Tianjin (CN); Lixin Wang, Tianjin (CN)

(73) Assignee: Zhejiang Jiuzhou Pharma Science & Technology Co., Ltd., Hangzhou, Zhejiang (CN)

( * ) Notice: Subject to any disclaimer, the term of this patent is extended or adjusted under 35 U.S.C. 154(b) by 0 days.

(21) Appl. No.: 13/885,051

(22) PCT Filed: Nov. 18, 2011

(86) PCT No.: PCT/CN2011/082432
§ 371 (c)(1),
(2), (4) Date: May 13, 2013

(87) PCT Pub. No.: WO2012/065571
PCT Pub. Date: May 24, 2012

(65) Prior Publication Data
US 2013/0225822 A1    Aug. 29, 2013

(30) Foreign Application Priority Data

Nov. 19, 2010   (CN) .......................... 2010 1 0550836

(51) Int. Cl.
| | | |
|---|---|---|
| C07F 9/06 | (2006.01) | |
| B01J 31/24 | (2006.01) | |
| B01J 31/18 | (2006.01) | |
| C07B 53/00 | (2006.01) | |
| C07C 29/145 | (2006.01) | |
| C07C 41/26 | (2006.01) | |
| C07C 67/31 | (2006.01) | |
| C07D 307/83 | (2006.01) | |
| C07F 9/58 | (2006.01) | |
| C07F 9/60 | (2006.01) | |
| C07B 41/02 | (2006.01) | |
| C07F 15/00 | (2006.01) | |

(52) U.S. Cl.
CPC .............. *B01J 31/249* (2013.01); *B01J 31/189* (2013.01); *C07B 53/00* (2013.01); *C07C 29/145* (2013.01); *C07C 41/26* (2013.01); *C07C 67/31* (2013.01); *C07D 307/83* (2013.01); *C07F 9/588* (2013.01); *C07F 9/60* (2013.01); *C07B 41/02* (2013.01); *C07F 15/004* (2013.01); *B01J 2231/643* (2013.01); *B01J 2531/827* (2013.01); *C07B 2200/07* (2013.01); *C07C 2101/14* (2013.01); *C07C 2102/08* (2013.01); *C07C 2102/10* (2013.01)
USPC ........................................................ 546/22

(58) Field of Classification Search
None
See application file for complete search history.

(56) References Cited

FOREIGN PATENT DOCUMENTS

| | | |
|---|---|---|
| CN | 1439643 | 9/2003 |
| CN | 101671365 | 3/2010 |
| CN | 102040625 | 5/2011 |
| WO | WO 01/00581 | 1/2001 |
| WO | WO 2009/129700 | 10/2009 |

OTHER PUBLICATIONS

Extended European Search Report for European Application No. 11842107.2 mailed Apr. 22, 2014.
Office Action for Japanese Patent Application No. 2013-539127 mailed Jul. 8, 2014. (English Translation).
Xie et al., "Chiral Iridium Catalysts Bearing Spiro Pyridine-Aminophosphine Ligands Enable Highly Efficient Asymmetric Hydrogenation of β-Aryl β-Ketoesters", *Angew. Chem. Int. Ed.*, vol. 51, 2012, pp. 201-203.

(Continued)

*Primary Examiner* — Heidi Reese
(74) *Attorney, Agent, or Firm* — Merchant & Gould P.C.

(57) ABSTRACT

The present invention relates to a chiral spiro-pyridylamidophosphine ligand compound, synthesis method therefor and application thereof. The chiral spiro-pyridylamidophosphine compound is a compound having a structure of Formula (I), a racemate or optical isomer thereof, or a catalytically acceptable salt thereof, and is mainly characterized by having a chiral spiro-dihydro-indene skeleton in its structure. The chiral spiro-pyridylamidophosphine compound may be synthesized with optical active 7-diaryl/alkylphosphino-7'-amino-1,1'-spiro-dihydro-indene or substituted 7-diaryl/alkylphosphino-7'-amino-1,1'-spiro-dihydro-indene having a spiro-skeleton as chiral starting material. The chiral spiro-pyridylamidophosphine compound may be used as a chiral ligand in asymmetric hydrogenation of a carbonyl compound catalyzed by iridium, in which the reaction activity is very high, the amount of the catalyst may be 0.0001 mol %, and the enantioselectivity of the reaction is up to 99.9% ee.

(I)

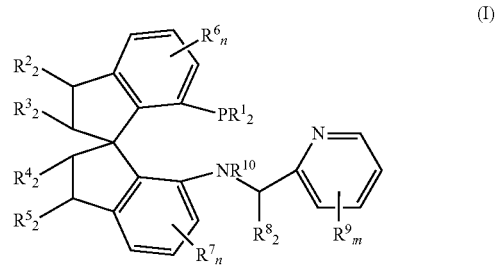

20 Claims, No Drawings

(56) References Cited

OTHER PUBLICATIONS

Abdur-Rashid et al., "Synthesis of Ruthenium Hydride Complexes Containing beta-Aminophosphine Ligands Derived from Amino Acids and their use in the $H_2$-Hydrogenation of Ketones and Imines", *Adv. Synth Catal.*, vol. 347, 2005, pp. 571-579.

Amoroso et al., "Aminophosphine Catalysts in Modern Asymmetric Synthesis", *AldrichimicaACTA*, vol. 41, No. 1, 2008, pp. 15-26.

Chen et al., "Ferrocene-based aminophosphine ligands in the Ru(II)-catalysed asymmetric hydrogenation of ketones: assessment of the relative importance of planar versus carbon-centred chirality", *Tetrahedron: Asymmetry*, vol. 17, 2006, pp. 1161-1164.

Dahlenburg et al., "Functional phosphines XII. Heterolytic $H_2$ cleavage and homogeneous >C=O hydrogenation catalyzed by platinum metal β-aminophosphine complexes", *Inorganic Chemistry Communication*, vol. 6, 2003, pp. 443-446.

Dahlenburg et al., "Iridium Complexes with Chiral and Achiral β-Aminophosphone Ligands: Catalysts for >C=O Hydrogenation and H/D Exchange Involving both Homo- and Heterolytic $H_2$ Activation", *Eur. J. Inorg. Chem.*, 2004, pp. 888-905.

Guo et al., "Asymmetric Hydrogenation of Ketones Catalyzed by Ruthenium Hydride Complexes of a Beta-aminophosphine Ligand Derived from Norephedrine", *Organonetakkucs*, vol. 23, 2004, pp. 5524-5529.

Guo et al., "Enantioselective Tandem Michal Addition/$H_2$-Hydrogenation Catalyzed by Ruthenium Hydride Borohydride Complexes Containing β-aminophosphine Ligands", *J. Am. Chem. Soc.*, vol. 127, 2005, pp. 516-517.

International Search Report for International Application No. PCT/CN2011/082432 mailed Mar. 1, 2012.

Okhuma et al., "Asymmetric Hydrogenation of Alkenyl, Cyclopropyl, and Aryl Ketones. $RuCl_2$(xylbinap)(1,2-diamine) as a Precatalyst Exhibiting a Wide Scope", *J. Am. Chem. Soc.*, vol. 120, 1998, pp. 13529-13530.

Ohkuma et al., "Practical Enantioselective Hydrogenation of Aromatic Ketones", *J. Am. Chem. Soc.*, vol. 117, 1995, pp. 2675-2676.

Xie et al., "Highly Enantioselective Hydrogenation of α-Arylmethylene Cycloalkanones Catalyzed by Iridium Complexes of Chiral Spiro Aminophosphine Ligands", *J. Am. Chem. Soc.*, vol. 132, 2010, pp. 4538-4539.

Xie et al., "An Additional Coordination Group Leads to Extremely Efficient Chiral Iridium Catalysts for Asymmetric Hydrogenation of Ketones", *Angew. Chem. Int. Ed.*, vol. 50, 2011, pp. 7329-7332.

CHIRAL SPIRO-PYRIDYLAMIDOPHOSPHINE LIGAND COMPOUND, SYNTHESIS METHOD THEREFOR AND APPLICATION THEREOF

The present application is a National Stage Application of PCT/CN2011/082432, filed Nov. 18, 2011, which claims benefit of application No. 201010550836.0, filed on Nov. 19, 2010 in China, titled "Chiral spiro-pyridylamidophosphine ligand compound, synthesis method therefor and application thereof", which applications are incorporated herein by reference. To the extent appropriate, a claim of priority is made to each of the above disclosed applications.

FIELD OF INVENTION

The present invention relates to a chiral spiro-pyridylamidophosphine ligand compound, synthesis method therefor and application thereof. Said chiral spiro-amidophosphine compound can be used in an asymmetric organic reaction as a chiral ligand. The present invention further provides a method for preparing the novel spiro-pyridylamidophosphine ligand, which is used in the asymmetric hydrogenation reaction of carbonyl compounds to prepare compounds of optical activity.

BACKGROUND OF THE INVENTION

In organic synthesis reactions, the chiral phosphine-nitrogen ligand of the containing amido coordination group is one of the most important chiral ligands. Such chiral phosphine-nitrogen ligands can coordinate with many transition metals to form chiral catalysts that are of great use in the asymmetric catalytic reaction. At present, such transition metal catalysts of chiral phosphine-nitrogen ligand containing amido coordination group have shown excellent reaction activity and enantioselectivity in a large number of asymmetric catalytic reactions (Amoroso, D.; Graham, T. W.; Guo, R.; Tsang, C.-W.; Abdur-Rashid, K. Aldrich. Chimica Acta. 2008, 41, 15).

More recently, due to the development of highly efficient chiral ruthenium-diphosphine/diamine catalysts by Noyori et al. ((a) Ohkuma, T.; Ooka, H.; Hashiguchi, S.; Ikariya, T.; Noyori, R. J. Am. Chem. Soc. 1995, 117, 2675; (b) Ohkuma, T.; Koizumi, M.; Doucet, H.; Pham, T.; Kozawa, M.; Murata, K.; Katayama, E.; Yokozawa, T.; Ikariya, T.; Noyori, R. J. Am. Chem. Soc. 1998, 120, 13529), extremely high catalytic activity and enantioselectivity have been achieved in the asymmetric hydrogenation reaction of non-functionalized ketones which is quite difficult in the past, resulting in close attention to such chiral catalysts. Although quite high enantioselectivity (>99% ee) and reaction activity (S/C>100,000) have been realized in a series of asymmetric catalytic hydrogenations of aromatic ketones, heterocyclic aromatic ketones, α,β-unsaturated ketones by such chiral catalysts, excellent result can be obtained only if the chiral and stereoscopic effect of the chiral diphosphine ligand and diamine ligand are both precisely matched. Therefore, in recent years, research has been focused on the chiral amidophosphine ligand containing amido group, especially containing hydrogen atom on the nitrogen atom, with advantages such as simple synthesis, flexible coordination and having the features of chiral phosphine ligand and amido ligand.

A series of amidophosphine ligands containing $NH_2$ coordination group have been reported by Morris et al. From University of Toronto, Canada in around 2004, and better hydrogenation has been accomplished by the ruthenium complexes with these chiral ligands in the asymmetric catalytic hydrogenation of ketones, imides etc. ((a) Abdur-Rashid, K.; Guo, R.; Lough, A. J.; Morris, R. H.; Song, D. Adv. Synth. Catal. 2005, 347, 571; (b) Guo, R.; Lough, A. J.; Morris, R. H.; Song, D. Organometallics, 2004, 23, 5524; (c) Guo, R.; Morris, R. H.; Song, D. J. Am. Chem. Soc. 2005, 127, 516). It has been reported by Chen's group from University of Liverpool, UK that moderate enantioselectivity (<79% ee) has been achieved in the asymmetric catalytic hydrogenation reaction of aryl alkyl ketones catalyzed by the ruthenium complex with chiral amidophosphine ligand having ferrocene skeleton (Chen, W.; Mbafor, W.; Roberts, S. M.; Whittall, J. Tetrahedron: Asymmetry, 2006, 17, 1161). It has also been reported by Dahlenburg's group from University of Erlangen-Nuremberg, Germany that moderate ee value was obtained in the simple ketone hydrogenation reaction catalyzed by iridium, rhodium complex with chiral amidophosphine ligand derived from β-amido alcohols ((a) Dahlenburg, L.; Götz, R. Eur. J. Inorg. Chem. 2004, 888; (b) Dahlenburg, L.; Gotz, R. Inorg. Chem. Commun. 2003, 6, 443). However, the enantioselectivity of these reported chiral catalysts of the chiral amidophosphine ligands in the asymmetric catalytic hydrogenation of simple ketones is much inferior to those chiral ruthenium-diphosphine/diamine catalysts developed by Noyori et al.

Recently, a series of bidentate chiral spiro-amidophosphine ligands containing aromatic amido group has been designed and synthesized by our group (Jian-Bo Xie, Jian-Hua Xie, Xiao-Yan Liu, Wei-Ling Kong, Shen Li, Qi-Lin Zhou, J. Am. Chem. Soc. 2010, 132, 4538; Qi-Lin Zhou, Jian-Hua Xie, Jian-Bo Xie, Li-Xin Wang, C N 101671365A). Better reaction activity and enantioselectivity have been achieved in the asymmetric catalytic hydrogenation of α,β-unsaturated ketones having exocyclic double bond by the iridium catalysts with such chiral amidophosphine ligands compared with the chiral ruthenium-diphosphine/diamine catalyst; excellent performance has also been observed in the asymmetric catalytic hydrogenation of simple aryl alkyl ketones. However, for this catalyst, the conversion number is still relatively low; although its conversion number (the ratio of substrate to catalyst) in the catalytic hydrogenation reaction of simple ketones and α,β-unsaturated ketones is much higher than that of other chiral catalysts, the maximum value is only 10,000, which is still needed to be further improved.

In the field of asymmetric catalytic hydrogenation reaction, there are only a few chiral catalysts developed with truly high efficiency. The development of highly efficient chiral ligand with simple synthesis and flexible coordination as well as its catalyst remains difficult and challenge in the asymmetric catalysis area.

DESCRIPTION OF THE INVENTION

The objective of the present invention is to provide a novel chiral spiro-pyridylamidophosphine ligand compound, synthesis method therefor and application thereof, and the chiral spiro-pyridylamidophosphine compound can be used as a chiral ligand in the iridium-catalyzed asymmetric catalytic hydrogenation reaction of carbonyl compounds, i.e., extremely high yield (>90%) and enantioselectivity (up to 99.9% ee) have been achieved in the iridium-catalyzed asymmetric hydrogenation reaction of carbonyl compounds including aryl alkyl ketones, ketenes and keto esters. The reaction has very high activity, in which the amount of catalyst used can be reduced to 0.0001% mol. The synthesis process in the present invention is simple, and has a high yield; and the resulting chiral spiro-pyridylamidophosphine compound is a very efficient chiral ligand.

The chiral spiro-pyridylamidophosphine ligand provided herein is a compound having a structure of Formula (I),

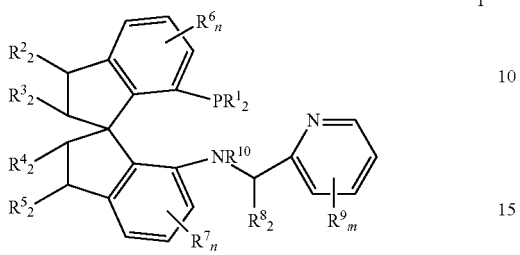

I or a racemate or optical isomer thereof, or a catalytically acceptable salt thereof, wherein, $R^1$ is $C_1$-$C_8$ chain hydrocarbyl or saturated cyclic hydrocarbyl or cycloalkenyl, phenyl, substituted phenyl, 1-naphthyl, 2-naphthyl, heteroaryl, furyl or thienyl, and the substituent on said substituted phenyl is halogen, $C_1$-$C_8$ alkyl or alkoxy, with a substituent amount of 1-5, and said heteroaryl is pyridyl;

$R^2$, $R^3$, $R^4$ and $R^5$ are H, $C_1$-$C_8$ alkyl or alkoxy, phenyl, substituted phenyl, 1-naphthyl, 2-naphthyl, heteroaryl, furyl or thienyl, and the substituent on said substituted phenyl is $C_1$-$C_8$ hydrocarbyl, alkoxy, with a substituent amount of 1-5, and said heteroaryl is pyridyl; or $R^2$-$R^3$, $R^4$-$R^5$ are incorporated into $C_3$-$C_7$ aliphatic ring, aromatic ring; $R^2$, $R^3$, $R^4$ and $R^5$ can be the same or different;

$R^6$, $R^7$ are selected from the group consisting of H, $C_1$-$C_8$ alkyl, $C_1$-$C_8$ alkoxy, $C_1$-$C_8$ aliphatic amido group, and n=0-3; or when n≥2, two adjacent $R^6$ groups or two adjacent $R^7$ groups can be incorporated into a $C_3$-$C_7$ aliphatic ring or aromatic ring, and $R^6$, $R^7$ can be the same or different;

$R^8$, $R^9$ are H, halogen, $C_1$-$C_8$ alkyl, $C_1$-$C_8$ alkoxy, phenyl, substituted phenyl, 1-naphthyl, 2-naphthyl, heteroaryl, furyl or thienyl, and the substituent on said substituted phenyl is halogen, $C_1$-$C_8$ alkyl, alkoxy, with a substituent amount of 1-5, and said heteroaryl is pyridyl, and m=0-3; or when m≥2, adjacent $R^9$ or $R^8$ and $R^9$ groups can be incorporated into a $C_3$-$C_7$ aliphatic ring or aromatic ring, and $R^8$, $R^9$ can be the same or different;

$R^{10}$ is H, $C_1$-$C_8$ alkyl, phenyl, substituted phenyl, 1-naphthyl, 2-naphthyl, heteroaryl, furyl or thienyl, and the substituent on said substituted phenyl is $C_1$-$C_8$ alkyl, alkoxy, with a substituent amount of 1-5, and said heteroaryl is pyridyl;

Preferably, in the structural Formula (I) of the compound described herein, $R^2$, $R^3$, $R^4$, $R^5$, $R^6$, $R^7$, $R^8$ and $R^{10}$ are H simultaneously, and $R^1$ is phenyl or substituted phenyl, and the substituent on said substituted phenyl is halogen, $C_1$-$C_8$ hydrocarbyl and alkoxy, with a substituent amount of 1-5; $R^9$ is H, halogen, $C_1$-$C_8$ alkyl, $C_1$-$C_8$ alkoxy, phenyl, substituted phenyl, 1-naphthyl, 2-naphthyl, heteroaryl, furyl or thienyl, and the substituent on said substituted phenyl is halogen, $C_1$-$C_8$ alkyl or alkoxy, with a substituent amount of 1-5, and said heteroaryl is pyridyl, and m=0-3; or when m≥2, adjacent $R^9$ groups can be incorporated into $C_3$-$C_7$ aliphatic ring or aromatic ring.

The present invention further specifically provides typical compounds of chiral spiro-pyridylamidophosphine ligand having the structures as follows, or racemate or optical isomer thereof, or catalytically acceptable salt thereof:

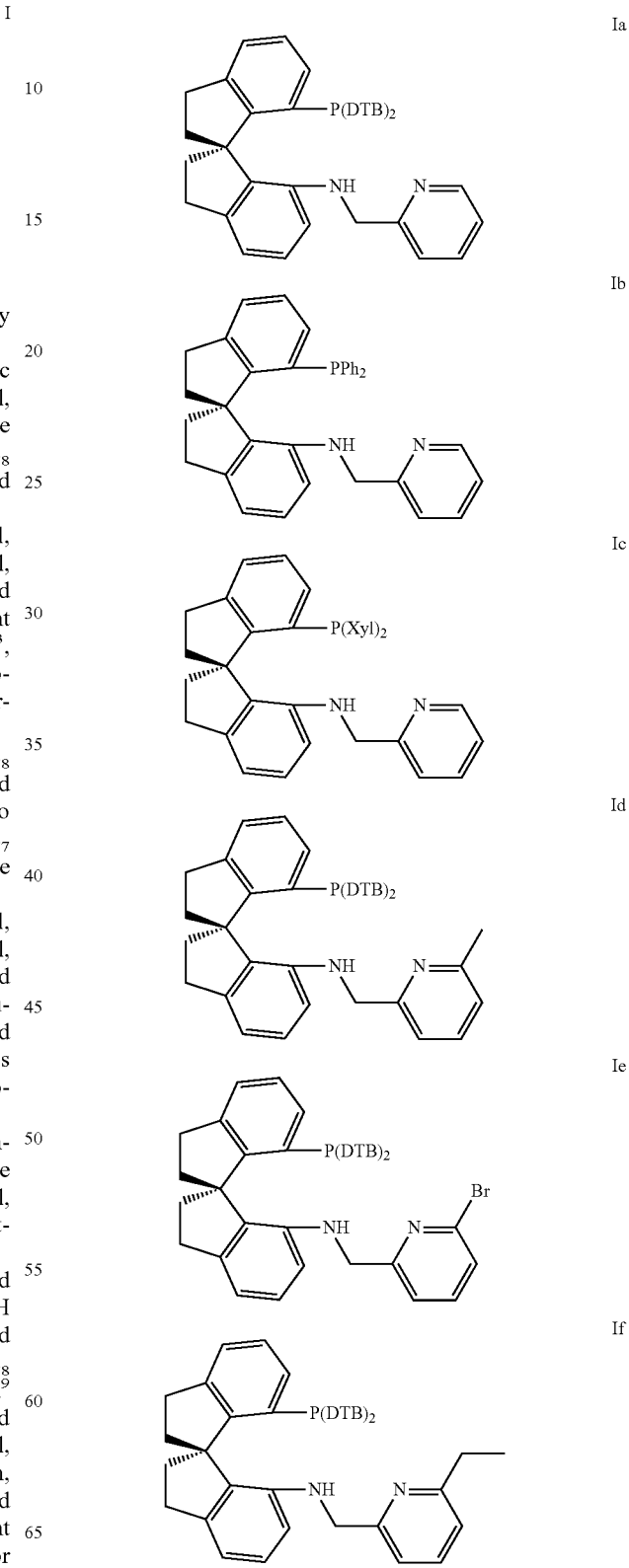

-continued

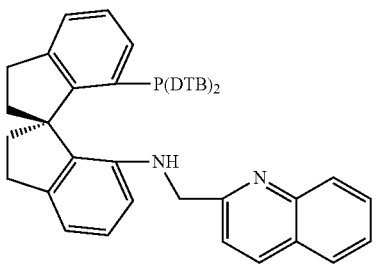

Ig

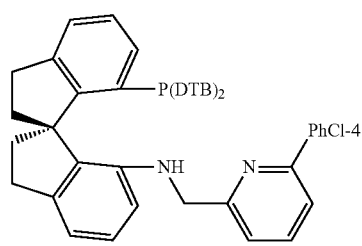

Ih

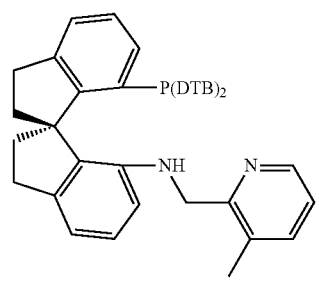

Ii

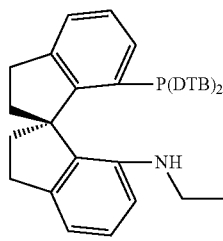

wherein DTB is:

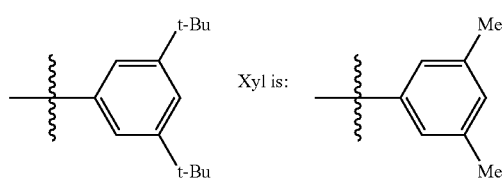

Xyl is:

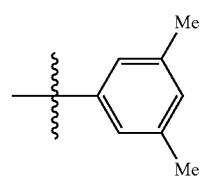

The present invention further provides the synthesis methods for said chiral spiro-pyridylamidophosphine compound, which are characterized by preparation through the following reactions using racemically or optically active compound 7-diaryl/alkylphosphino-7'-amino-1,1'-spiro-dihydro-indene shown as Formula (II) having a chiral spiro-dihydro-indene skeleton as the starting material:

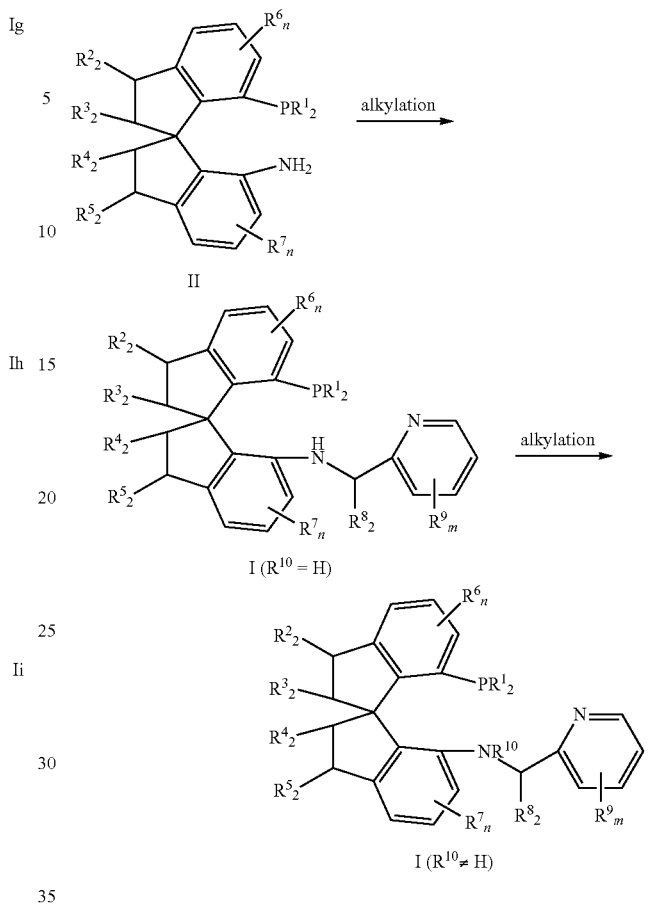

wherein, $R^1$-$R^{10}$ and the values of n and m are defined as claim 1, wherein, the racemically or optically active compound 7-diaryl/alkylphosphino-7'-amino-1,1'-spiro-dihydro-indene of Formula (II) is synthesized by the method according to references (Jian-Bo Xie, Jian-Hua Xie, Xiao-Yan Liu, Wei-Ling Kong, Shen Li, Qi-Lin Zhou, *J. Am. Chem. Soc.* 2010, 132, 4538; Qi-Lin Zhou, Jian-Hua Xie, Jian-Bo Xie, Li-Xin Wang, C N 101671365A).

The specific synthesis method for the chiral spiro-pyridylamidophosphine compound I is described as below:

Step 1:

Synthesis method 1: racemically or optically active 7-diaryl/alkylphosphino-7'-amino-1,1'-spiro-dihydro-indene having the structure of Formula (II) is reacted with substituted pyridylaldehyde or pyridone in a reactor for 2-24 hours in the presence of organic solvent and reducing agent to obtain the spiro-pyridylamidophosphine compound I with one hydrogen atom on corresponding nitrogen atom ($R^{10}$=H); the molar ratio among said racemically or optically active 7-diaryl/alkylphosphino-7'-amino-1,1'-spiro-dihydro-indene II of Formula (II), pyridylaldehyde and reducing agent is in the range of 1:1-5:1-10; and the reaction temperature is 0-120° C.

Synthesis method 2: racemically or optically active 7-diaryl/alkylphosphino-7'-amino-1,1'-spiro-dihydro-indene having the structure of Formula (II) is initially reacted with pyridine formyl chloride in a reactor in the presence of organic solvent and alkali, to obtain a corresponding acylated compound, followed by reduction with a reducing agent to obtain the spiro-pyridylamidophosphine compound I with one hydrogen atom on corresponding nitrogen atom ($R^{10}$=H); in the acylation reaction, the molar ratio among said racemically or optically active 7-diaryl/alkylphosphino-7'-amino-1,1'-spiro-dihydro-indene II, pyridine formyl chloride and alkali is in the range of 1:1-5:1-10; and the reaction temperature is 0-100° C. During the reduction reaction, the molar ratio of the resulting acylated compound to the reducing agent is in the range of 1:1-10, and the reaction temperature is from −20 to 100° C.

Synthesis method 3: racemically or optically active 7-diaryl/alkylphosphino-7'-amino-1,1'-spiro-dihydro-indene having the structure of Formula (II) is initially reacted with pyridine formic acid in a reactor in the presence of organic solvent, alkali and carboxyl-activating reagent to obtain a corresponding acylated compound, followed by reduction with a reducing agent to obtain the spiro-pyridylamidophosphine compound I with one hydrogen atom on corresponding nitrogen atom ($R^{10}$=H); in the acylation reaction, the molar ratio among said racemically or optically active 7-diaryl/alkylphosphino-7'-amino-1,1'-spiro-dihydro-indene II, pyridine formic acid and activating reagent is in the range of 1:1-5:1-10, and the reaction temperature is from −30 to 100° C.; in the reduction reaction, the molar ratio of the resulting acylated compound to the reducing agent is in the range of 1:1-10, and the reaction temperature is from −20 to 100° C.

Step 2: according to the synthesis method or step mentioned above, using the resulting spiro-pyridylamidophosphine compound I with one hydrogen atom contained on the nitrogen atom ($R^{10}$=H) as the starting material, the spiro-pyridylamidophosphine compound I with no hydrogen atom on the nitrogen atom ($R^{10}$≠H) can be synthesized by replacing the pyridylaldehyde, pyridine formyl chloride, pyridine formic acid described above with fatty aldehyde or aromatic aldehyde, acyl chloride and carboxylic acid.

In the above synthesis method, the molecular formula of said substituted pyridylaldehyde, pyridone, pyridine formyl chloride, pyridine formic acid and the fatty aldehyde or the aromatic aldehyde, acyl chloride, carboxylic acid are defined by the $R^8$-$R^{10}$ in the Formula (I) and the values of m. Said organic solvent can be any one of methanol, ethanol, propanol, isopropanol, butanol, tetrahydrofuran, toluene, xylene, methyl tert-butyl ether, diethyl ether, dioxane, N,N-dimethyl formamide, dimethyl sulfoxide, or any mixture thereof; said reducing agent can be lithium aluminium hydride, sodium borohydride, sodium triacetyl borohydride or sodium cyanoborohydride; said alkali is an organic base or an inorganic base, in which said organic base can be pyridine, triethylamine, tributyl amine, N-methylmorpholine or N,N-diethyl isopropyl amine; said inorganic base can be sodium hydroxide, potassium hydroxide, sodium carbonate or potassium carbonate; said carboxyl-activating reagent is ethyl chloroformate, isopropyl chloroformate, N,N'-dicyclohexylcarbodiimide or carbonyl diimidazole.

The chiral spiro-pyridylamidophosphine compound according to the present invention can be used in the asymmetric catalytic reaction as a chiral ligand, in which corresponding transition metal complexes can be formed by the compound as the chiral ligand together with the metal precursor of transition metals such as rhodium, ruthenium, iridium, palladium, copper, iron, nickel etc., and the chiral catalyst is formed and used in the asymmetric reaction, especially in the iridium-catalyzed asymmetric catalytic hydrogenation reaction of carbonyl compounds including aryl alkyl ketone, ketene and keto ester, which allows for the production of chiral alcohol compounds, that are of important use in the chiral pharmaceutical synthesis, the important chiral organic compound synthesis and the biologically active natural product synthesis, in an almost quantitative yield, and with excellent reaction activity and enantioselectivity. The preparation reaction of said chiral catalyst is described below:

hydrogenated chiral catalyst is obtained by the initial 0.5-4 hours of complexation reaction of the chiral spiro-pyridylamidophosphine compound and iridium catalyst precursor in an organic solvent at 25-120° C., followed by 0.1-3 hours of reaction stirred under the hydrogen atmosphere at the pressure of 0.1-10 Mpa; or complexation reaction between chiral spiro-pyridylamidophosphine compound and iridium catalyst precursor is performed in an organic solvent for 0.5-4 hours, then desolventization is performed to obtain the corresponding complex, which is then subjected to reaction under stirring in the organic solvent under the hydrogen atmosphere at the pressure of 0.1-10 Mpa for 0.1-3 hours, to obtain the chiral catalyst.

The molar ratio of said iridium catalyst precursor to the chiral spiro-amidophosphine ligand is in the range from 1:1.2 to 1:1.5 (Ir/L); said iridium catalyst precursor is [Ir(cod)]Cl$_2$ (cod=Cyclooctadiene), [Ir(cod)$_2$]BF$_4$, [Ir(cod)$_2$]PF$_6$, [Ir(cod)$_2$]SbF$_6$ or [Ir(cod)$_2$] OTf.

The chiral catalyst prepared can be used for the asymmetric catalytic hydrogenation reaction of carbonyl compound, and the reaction is described below:

In an organic solvent, the resulting reaction solution or solid mentioned above is reacted as the catalyst with the carbonyl compound and the alkali added by stirring under the hydrogen atmosphere at the pressure of 0.1-10 Mpa for 0.1-24 hours, to obtain the chiral alcohol compounds.

The amount of said catalyst used is 0.0001-5 mol %. The concentration of the substrate is 0.001-10.0 M. Said alkali is sodium hydroxide, potassium hydroxide, sodium carbonate, potassium carbonate, sodium ethoxide, potassium ethoxide, sodium tert-butoxide, potassium tert-butoxide, lithium tert-butoxide, triethyl amine, tributyl amine or N-methyl morpholine. The concentration of the alkali is 0.005 M-1.0 M, and the reaction temperature is 0-80° C.

The above organic solvent is any one of methanol, ethanol, propanol, isopropanol, butanol, tetrahydrofuran, toluene, methyl tert-butyl ether, dioxane, DMF, DMSO, or any mixture thereof.

The chiral spiro-pyridylamidophosphine compound provided herein is a compound having the structure of Formula (I), or a racemate or optical isomer thereof, or a catalytically acceptable salt thereof, and the main structural characteristic thereof is the chiral spiro-dihydro-indene skeleton. It can be used as the chiral ligand in the iridium-catalyzed asymmetric catalytic hydrogenation reaction of carbonyl compounds, and an extremely high yield (>90%) and enantioselectivity (up to 99.9% ee) have been achieved in the iridium-catalyzed asymmetric hydrogenation reaction of carbonyl compounds including aryl alkyl ketones, ketenes and keto esters. The reaction has very high activity, in which the amount of catalyst used can be reduced to 0.0001% mol. The synthesis process in the present invention is simple, with a high yield; and the resulting chiral spiro-pyridylamidophosphine compound is a very efficient chiral ligand.

SPECIFIC MODES FOR CARRYING OUT THE INVENTION

In order to further understand the present invention, preferable embodiments of the present invention will be described by reference to the examples, but it should be appreciated that these descriptions are merely intended to further illustrate the features and advantages of the present invention, rather than limiting the claims of the invention.

The results of the present invention are illustrated by the specific examples below, but the scope of the present invention is not limited by the following Examples.

Example 1

Synthesis of (R)-N-(pyridyl-2-methyl)-7-di-(3,5-di-tert-butylphenyl)phosphino-7-amino-1,1'-spiro-dihydro-indene (Ia)

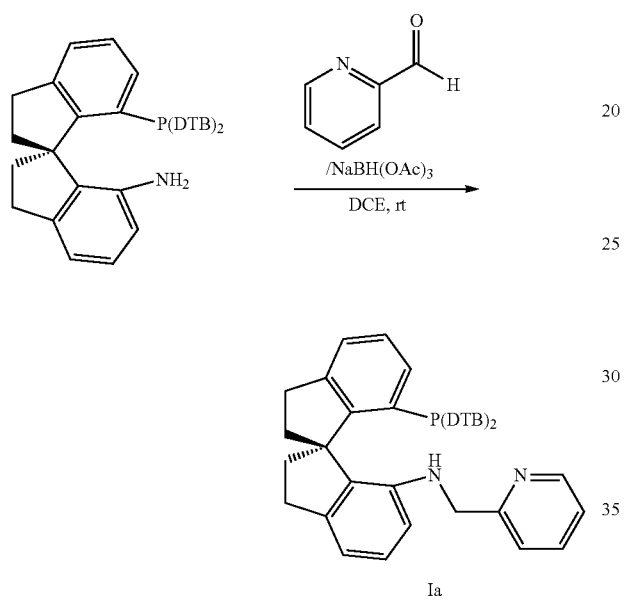

Ia

Under nitrogen atmosphere, (R)-7-di-(3,5-di-tert-butylphenyl)phosphino-T-amino-1,1'-spiro-dihydro-indene (966 mg, 1.5 mmol), sodium triacetoxyborohydride (509 mg, 2.4 mmol) and 6 ml 1,2-dichloroethane were weighed into a 50 ml dry two-neck bottle. After the solid was dissolved by stirring at room temperature, pyridylaldehyde was added (161 mg, 1.5 mmol). After the reaction was stirred for 6 h at room temperature, the starting material was almost consumed (monitored by TLC, petroleum ether:ethyl acetate=7:1). The reaction was quenched by saturated aqueous solution of sodium bicarbonate, extracted by ethyl acetate, and dried by anhydrous magnesium sulfate. After desolventization, 1.01 g white solid was obtained by purification of the resulting solid through silica gel column chromatography (petroleum ether: ethyl acetate=10:1, 2% triethylamine), with a yield of 92%.

Mp 172-174° C.; [α]$D^{20}$+172 (c 0.5, CH$_2$Cl$_2$); $^1$H NMR (400 mhz, cdcl$_3$) δ 8.30 (d, J=4.8 Hz, 1H, Ar—H), 7.44-7.39 (m, 1H, Ar—H), 7.31 (d, J=7.2 Hz, 1H, Ar—H), 7.26-7.19 (m, 3H, Ar—H), 7.12-7.06 (m, 2H, Ar—H), 7.02-6.99 (m, 1H, Ar—H), 6.88-6.84 (m, 3H, Ar—H), 6.77-6.75 (dd, J=1.6, 7.6 Hz, 2H, Ar—H), 6.68 (d, J=9.2 Hz, 1H, Ar—H), 6.10 (d, J=8.0 Hz, 1H, Ar—H), 4.20 (t, J=5.2 Hz, 1H), 3.97 (dd, J=6, 16.4 Hz, 1H), 3.73 (dd, J=4.4, 16.4 Hz, 1H), 3.13-2.76 (m, 4H), 2.49-2.40 (m, 1H), 2.19-2.09 (m, 3H), 1.09 (s, 18H), 1.16 (s, 18H); $^{31}$P NMR (162 mhz, cdcl$_3$) δ −18.17 (s); $^{13}$C NMR (100 mhz, cdcl$_3$) δ 155.8, 152.5 (d, J=24.3 Hz), 149.9 (d, J=6.3 Hz), 148.9, 144.3, 144.2, 144.1, 138.2 (d, J=11.7 Hz), 136.1, 135.2, 134.9, 133.8, 132.6 (d, J=3.4 Hz), 128.4, 128.1, 128.0, 127.9, 126.9, 125.7, 122.2, 121.5, 121.5, 120.7, 113.9, 108.6, 61.7 (d, J=3.3 Hz), 48.5, 38.6 (d, J=3.4 Hz), 36.1, 34.7 (d, J=3.8 Hz), 31.4 (d, J=2.4 Hz), 30.92, 31.36. HRMS (ESI) calcd for C$_{51}$H$_{63}$N$_2$P [M+H]$^+$: 735.4802. Found: 735.4804.

(In the following Examples, Compounds Ib-Ij were prepared via the same process as Example 1 except for the reactants changed).

Example 2

Synthesis of (R)-N-(pyridyl-2-methyl)-7-diphenylphosphino-7'-amino-1,1'-spiro-dihydro-indene (Ib)

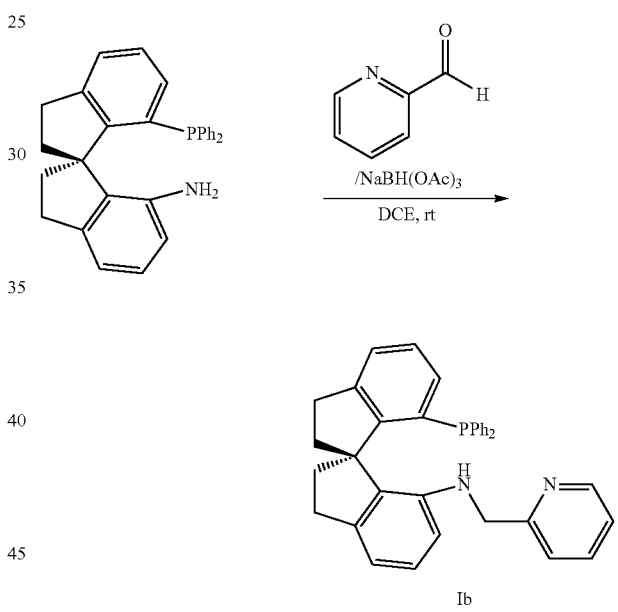

Ib

Specific process can be found in Example 1, and white solid was obtained with a yield of 85%.

Mp 172-174° C.; [α]$D^{20}$+265 (c 0.5, CH$_2$Cl$_2$), $^1$HNMR (400 mhz, cdcl$_3$) δ 8.23 (d, J=3.6 Hz, 1H), 7.38 (t, J=6.8 Hz, 1H), 7.26-7.24 (m, 1H), 7.16-7.07 (m, 5H), 7.03-6.83 (m, 10H), 6.61 (d, J=7.2 Hz, 1H), 5.88 (d, J=8.0 Hz, 1H), 3.98 (brs, 1H), 3.82-3.77 (m, 1H), 3.56-3.51 (m, 1H), 3.02-2.92 (m, 4H), 2.42-2.30 (m, 2H), 2.25-2.22 (m, 1H), 2.12-2.08 (m, 1H); $^{31}$P NMR (162 mhz, cdcl$_3$) δ −22.47 (s); $^{13}$C NMR (100 mhz, cdcl$_3$) δ 157.6, 152.2, 151.9, 147.6, 143.4, 143.3, 142.3, 138.5, 138.4, 135.4, 135.3, 135.2, 133.4 (d, J=2.6 Hz), 133.0, 132.8, 132.2, 132.0, 131.9, 127.2 (d, J=4 Hz), 127.0 (d, J=5.7 Hz), 126.9, 126.8, 126.6, 126.3, 125.0, 120.4, 119.6, 112.7, 107.3, 64.8, 60.6 (d, J=3.2 Hz), 47.1, 38.5 (d, J=5.1 Hz), 35.0, 30.3, 29.9. HRMS (ESI) calcd for C$_{35}$H$_{31}$N$_2$P[M+H]$^+$: 511.2298. Found: 511.2296.

Example 3

Synthesis of (R)-N-(pyridyl-2-methyl)-7-di-(3,5-methylphenyl)phosphino-7'-amino-1,1'-spiro-dihydro-indene (Ic)

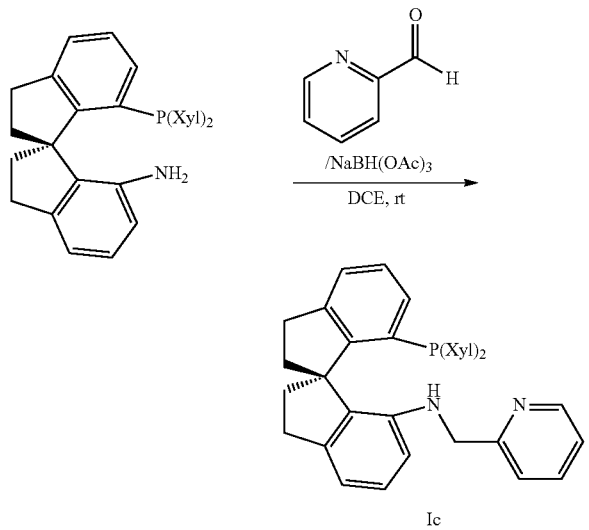

Specific process can be found in Example 1, and white solid was obtained with a yield of 82%.

Mp 172-174° C.; $[\alpha]_D^{20}$ +262 (c 0.5, CH$_2$Cl$_2$), $^1$H NMR (400 mhz, cdcl$_3$) δ 8.29 (d, J=4.4 Hz, 1H), 7.44-7.40 (m, 1H), 7.32-7.30 (m, 1H), 7.22 (t, J=7.2 Hz, 1H), 7.12-7.00 (m, 3H), 6.82-6.76 (m, 3H), 6.70 (d, J=7.6 Hz, 1H), 6.60 (d, J=7.6 Hz, 4H), 5.96 (d, J=7.6 Hz, 1H), 4.00-3.97 (m, 1H), 3.91-3.85 (m, 1H), 3.47 (dd, J=4, 16.4 Hz, 1H), 3.13-2.99 (m, 4H), 2.53-2.39 (m, 2H), 2.33-2.28 (m, 1H), 2.17 (s, 6H), 2.01 (s, 6H); $^{31}$P NMR (162 mhz, cdcl$_3$) δ −22.32 (s); $^{13}$C NMR (100 mhz, cdcl$_3$) δ 158.6, 153.1, 152.9, 148.7, 144.4, 144.3, 144.2, 143.6, 137.2 (d, J=6.0 Hz), 137.0 (d, J=7.8 Hz), 136.2, 134.4, 133.4, 132.2, 132.0, 131.0, 130.8, 130.1, 129.5, 128.0, 127.2, 125.7, 121.4, 120.5, 113.7, 108.4, 61.7, 48.0, 39.4 (d, J=5.4 Hz), 36.1., 31.4, 31.0, 21.4, 21.1. HRMS (ESI) calcd for C$_{39}$H$_{39}$N$_2$P[M+H]$^+$: 567.2924. Found: 567.2916.

Example 4

Synthesis of (R)-N-(6-methylpyridine-2-methyl)-7-di-(3,5-di-tert-butylphenyl)phosphino-7'-amino-1,1'-spiro-dihydro-indene (Id)

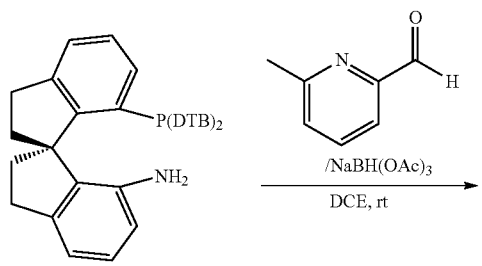

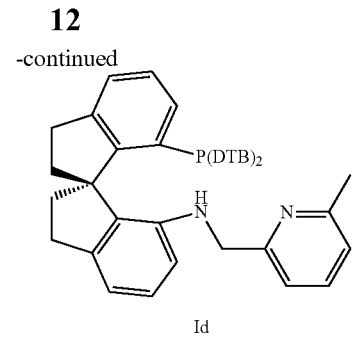

Specific process can be found in Example 1, and white solid was obtained with a yield of 95%.

Mp 153-155° C., $[\alpha]_D^{20}$ +191 (c 1.0, CH$_2$Cl$_2$), $^1$H NMR (400 mhz, cdcl$_3$) δ 7.32-7.28 (m, 2H), 7.24-7.17 (m, 3H), 7.14-7.08 (m, 2H), 6.87-6.83 (m, 3H), 6.77-6.75 (m, 2H), 6.68 (d, J=7.2 Hz, 1H), 6.59 (d, J=7.6 Hz, 1H), 6.17 (d, J=8 Hz, 1H), 4.27 (brs, 1H), 4.03 (dd, J=6.4, 16 Hz, 1H), 3.67-3.63 (m, 1H), 3.09-2.89 (m, 3H), 2.80-2.74 (m, 1H), 2.51-2.43 (m, 1H), 2.34 (s, 3H), 2.18-2.03 (m, 3H), 1.15 (s, 3H), 1.06 (s, 3H); $^{31}$P NMR (162 mhz, cdcl$_3$) δ −18.20 (s); $^{13}$C NMR (100 mhz, cdcl$_3$) δ 157.7, 157.5, 152.8, 152.6, 144.4, 144.3 (d, J=3.4 Hz), 144.0, (d, J=7.3 Hz), 138.2, 138.1, 136.4, 136.3, 136.1, 135.1, 134.8, 133.7, 132.3 (d, J=3.5 Hz), 128.4, 128.2, 128.1, 127.9, 127.8, 126.9, 125.8, 122.0, 121.5, 121.0, 117.6, 113.7, 108.6, 61.7 (d, J=3.3 Hz), 48.4, 38.6 (d, J=3.2 Hz), 35.8, 34.7, 34.6, 31.4, 31.3, 30.8, 24.5. HRMS (ESI) calcd for C$_{52}$H$_{65}$N$_2$P[M+H]$^+$: 749.4958. Found: 749.4952

Example 5

Synthesis of (R)-N-(6-bromopyridyl-2-methyl)-7-di-(3,5-di-tert-butylphenyl) phosphino-7'-amino-1,1'-spiro-dihydro-indene (Ie)

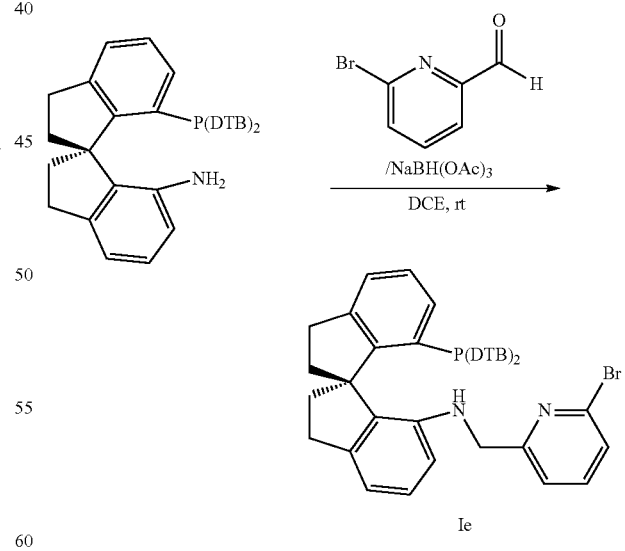

Specific process can be found in Example 1, and white solid was obtained with a yield of 81%.

Mp 84-85° C., $[\alpha]_D^{20}$ +216 (c 1.0, CH$_2$Cl$_2$), $^1$H NMR (400 mhz, cdcl$_3$) δ 7.33-7.31 (m, 1H), 7.28-7.20 (m, 5H), 7.13-7.05 (m, 2H), 6.88 (d, J=7.6 Hz, 2H), 6.82 (d, J=7.2 Hz, 1H), 6.75-6.70 (m, 3H), 6.04 (d, J=8 Hz, 1H), 3.92-3.82 (m, 2H), 3.71-3.66 (dd, J=4.4, 16.4 Hz, 1H), 3.10-2.92 (m, 3H), 2.83-2.77 (m, 1H), 2.42 (m, 1H), 2.20-2.11 (m, 3H), 1.15 (s, 18H), 1.13 (s, 18H); $^{31}$P NMR (162 mhz, cdcl$_3$) δ −18.52 (s); $^{13}$C NMR (100 mhz, cdcl$_3$) δ 160.1, 151.4 (d, J=24.5 Hz), 149.0, 148.9, 148.8, 148.7, 143.4, 142.9 (d, J=7.4 Hz), 142.5 (d, J=2.9 Hz), 140.2, 137.7, 137.1, 137.0, 135.0, 134.8, 133.9, 133.7, 132.7, 131.7 (d, J=3.2 Hz), 127.2, 127.0, 126.8, 126.1, 125.0, 124.8, 121.3, 120.4, 128.3, 113.3, 107.7, 60.6 (d, J=3.0 Hz), 47.2, 37.6, 34.9, 33.7 (d, J=2.9 Hz), 30.3, 30.1, 29.8. HRMS (ESI) calcd for c$_{51}$h$_{62}$brn$_2$p[M+H]$^+$: 813.3907. Found: 813.3906

Example 6

Synthesis of (R)-N-(6-ethylpyridyl-2-methyl)-7-di-(3,5-di-tert-butylphenyl) phosphino-7'-amino-1,1'-spiro-dihydro-indene (If)

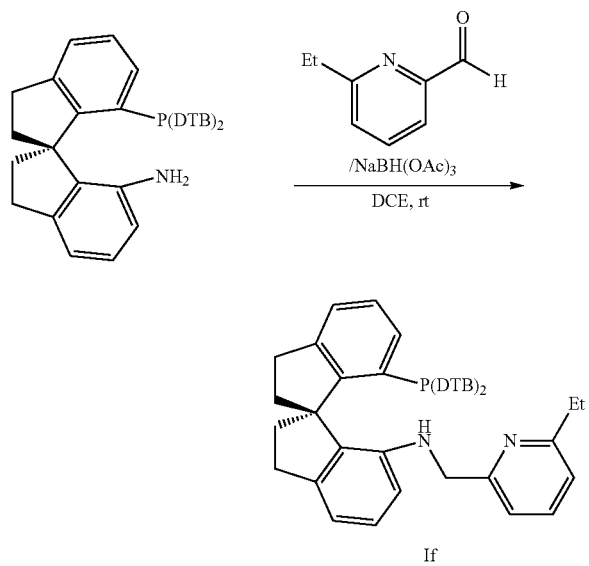

Specific process can be found in Example 1, and white solid was obtained with a yield of 92%.

Mp 79-80° C., [α]$_D^{20}$ +224 (c 1.0, CH$_2$Cl$_2$), $^1$H NMR (400 mhz, cdcl$_3$) δ 7.35-7.30 (m, 2H), 7.22-7.17 (m, 3H), 7.13-7.07 (m, 2H), 6.88-6.83 (m, 3H), 6.74 (d, J=7.6 Hz, 2H), 6.68 (d, J=7.2 Hz, 1H), 6.59 (d, J=8 Hz, 1H), 6.16 (d, J=7.6 Hz, 1H), 4.30-4.28 (m, 1H), 3.99 (dd, J=6.4, 16 Hz, 1H), 3.65-3.61 (m, 1H), 3.10-2.92 (m, 3H), 2.82-2.80 (m, 1H), 2.59 (q, J=7.6 Hz, 2H), 2.51-2.43 (m, 1H), 2.16-2.09 (m, 3H), 1.21-1.16 (m, 3H), 1.11 (s, 18H), 1.06 (s, 18H); $^{31}$P NMR (162 mhz, cdcl$_3$) δ −18.34 (s); $^{13}$C NMR (100 mhz, cdcl$_3$) δ 162.7, 157.5, 152.9, 152.6, 149.8 (d, J=6.2 Hz), 144.3 (d, J=2.8 Hz), 144.2 (d, J=3.2 Hz), 143.9, 143.8, 138.3, 138.1, 136.4, 136.2, 136.0, 134.9, 134.7, 133.7, 132.2 (d, J=3.5 Hz), 128.3, 128.1, 128.0, 127.9, 127.8, 126.9, 125.7, 122.0, 121.3, 119.5, 117.7, 113.6, 108.5, 61.6 (d, J=3.3 Hz), 48.3, 38.6 (d, J=3.1 Hz), 35.6, 34.7, 34.6, 31.3, 31.2, 31.1, 30.8, 14.4. HRMS (ESI) calcd for C$_{53}$H$_{67}$N$_2$P[M+H]$^+$: 763.5115. Found: 763.5116.

Example 7

Synthesis of (R)-N-(quinolyl-2-methyl)-7-di-(3,5-di-tert-butylphenyl)phosphino-7'-amino-1,1'-spiro-dihydro-indene (Ig)

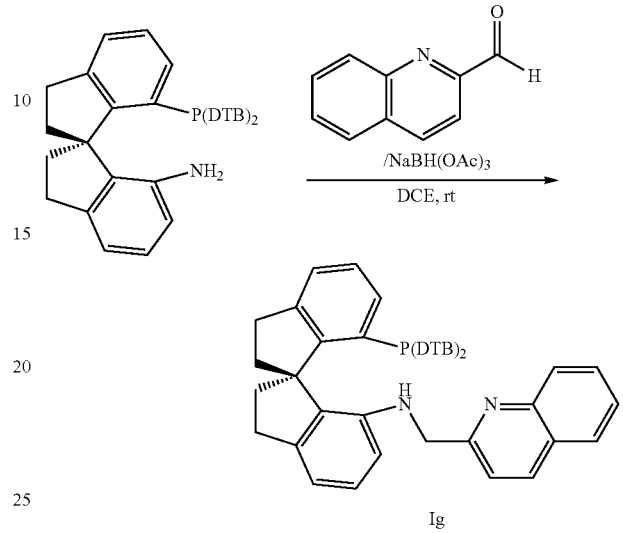

Specific process can be found in Example 1, and white solid was obtained with a yield of 100%.

Mp 97-99° C., [α]$_D^{20}$ +216 (c 1.0, CH$_2$Cl$_2$), $^1$H NMR (400 mhz, cdcl$_3$) δ 7.92 (d, J=8.4 Hz, 1H), 7.76-7.69 (m, 2H), 7.64-7.60 (m, 1H), 7.46-7.42 (m, 2H), 7.28-7.25 (m, 1H), 7.24-7.22 (m, 1H), 7.17-7.07 (m, 4H), 6.81-6.76 (m, 4H), 6.69 (d, J=6 Hz, 1H), 6.24 (d, J=7.6 Hz, 1H), 4.84-4.82 (m, 1H), 4.26 (dd, J=6.0, 16.4 Hz, 1H), 3.92 (dd, J=3.2, 16.8 Hz, 1H), 3.13-3.04 (m, 2H), 2.97-2.89 (m, 1H), 2.78-2.72 (m, 1H), 2.18-2.02 (m, 3H), 1.16 (s, 18H), 0.96 (s, 18H); $^{31}$P NMR (162 mhz, cdcl$_3$) δ −17.74 (s); $^{13}$C NMR (100 mhz, cdcl$_3$) δ 157.1, 151.8, 151.5, 148.8, 148.7, 148.6, 146.4, 143.4 (d, J=2.6 Hz), 143.2 (d, J=3.6 Hz), 143.1, 143.0, 137.0, 136.9, 135.4, 135.3, 134.9, 134.1, 133.8, 132.6, 131.0 (d, J=3.4 Hz), 128.3, 127.9, 127.3 (d, J=3.1 Hz), 127.1, 126.9, 126.7, 126.2, 126.1, 126.0, 124.7 (d, J=3.8 Hz), 120.7, 120.4, 118.4, 112.6, 107.3, 60.7 (d, J=3.2 Hz), 47.8, 37.5 (d, J=2.8 Hz), 34.7, 33.7, 33.5, 30.3, 30.1, 29.8. HRMS (ESI) calcd for C$_{55}$H$_{65}$N$_2$P[M+H]$^+$: 785.4958. Found: 785.4955.

Example 8

Synthesis of (R)-N-[6-(4-chlorophenyl)pyridyl-2-methyl]-7-di-(3,5-di-tert-butylphenyl) phosphino-7'-amino-1,1'-spiro-dihydro-indene (Ih)

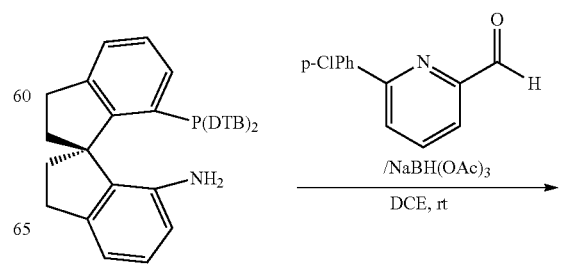

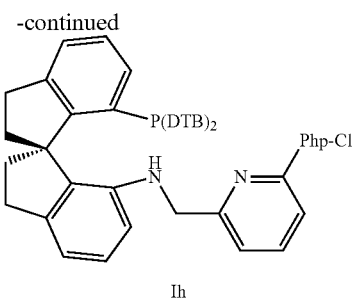

Specific process can be found in Example 1, and white solid was obtained with a yield of 96%.

Mp 96-98° C., $[\alpha]_D^{20}$ +204 (c 1.0, $CH_2Cl_2$), $^1H$ NMR (400 mhz, $cdcl_3$) δ 7.84 (d, J=8.0 Hz, 2H), 7.51-7.40 (m, 4H), 7.32 (brs, 1H), 7.26-7.24 (m, 2H), 7.21 (brs, 1H), 7.16-7.06 (m, 3H), 6.93 (d, J=8.0 Hz, 2H), 6.84 (d, J=7.6 Hz, 1H), 6.73-6.70 (m, 3H), 6.09 (d, J=8.0 Hz, 1H), 3.92-3.89 (m, 1H), 3.84-3.71 (m, 2H), 3.14-2.92 (m, 3H), 2.86-2.81 (m, 1H), 2.54-2.43 (m, 1H), 2.24-2.13 (m, 3H), 1.15 (s, 36H); $^{31}P$ NMR (162 mhz, $cdcl_3$) δ −19.06 (s); $^{13}C$ NMR (100 mhz, $cdcl_3$) δ 158.5, 154.0, 151.7, 151.5, 149.0 (d, J=6.7 Hz), 148.7 (d, J=5.8 Hz), 143.3 (d, J=2.7 Hz), 143.0 (d, J=3.2 Hz), 142.8 (d, J=7.4 Hz), 137.3, 137.2, 136.7, 136.1, 134.8, 134.7, 133.9, 133.7, 133.6, 132.9, 131.4 (d, J=3.5 Hz), 127.6, 127.2, 127.1, 127.0, 126.9 (d, J=7.6 Hz), 126.7, 125.9, 124.8, 121.4, 120.3, 118.2, 116.8, 113.0, 107.8, 60.6 (d, J=3.2 Hz), 48.1, 37.7 (d, J=3.7 Hz), 34.7, 33.7, 33.6, 30.3 (d, J=6.0 Hz), 30.1, 29.8. HRMS (ESI) calcd for $c_{57}h_{66}cln_2p[M+H]^+$: 845.4725. Found: 845.4729.

Example 9

Synthesis of (R)-N-(3-methylpyridyl-2-methyl)-7-di-(3,5-di-tert-butylphenyl) phosphino-7'-amino-1,1'-spiro-dihydro-indene (Ii)

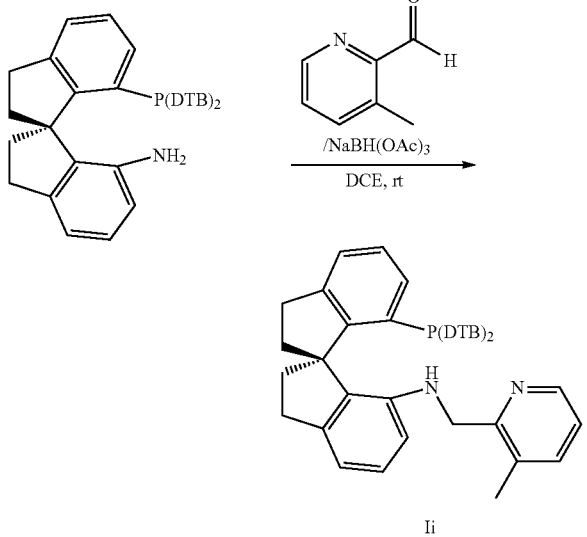

Specific process can be found in Example 1, and white solid was obtained with a yield of 96%.

Mp 160-161° C., $[\alpha]_D^{20}$ +213 (c 0.5, $CH_2Cl_2$), $^1H$ NMR (400 mhz, $cdcl_3$) δ 7.85 (d, J=4.4 Hz, 1H), 7.37 (d, J=7.2 Hz, 1H), 7.28-7.26 (m, 1H), 7.23-7.12 (m, 4H), 7.06-7.03 (m, 1H), 6.92-6.89 (m, 1H), 6.77 (d, J=7.6 Hz, 2H), 6.69-6.66 (m, 3H), 6.27 (d, J=8 Hz, 1H), 5.48 (d, J=5.6 Hz, 1H), 4.07 (dd, J=6, 16 Hz, 1H), 3.47 (d, J=16 Hz, 1H), 3.08-2.93 (m, 3H), 2.81-2.75 (m, 1H), 2.49-2.41 (m, 1H), 2.19-2.06 (m, 6H), 1.15 (s, 18H), 0.95 (s, 18H); $^{31}P$ NMR (162 mhz, $cdcl_3$) δ −17.55 (s); $^{13}C$ NMR (100 mhz, $cdcl_3$) δ 153.5, 151.4, 151.2, 148.7 (d, J=6 Hz), 148.4 (d, J=6.3 Hz), 144.5, 143.3, 143.2, 143.1, 137.4, 137.3, 135.7, 135.5, 133.7, 133.5, 132.5, 131.5 (d, J=3.5 Hz), 128.7, 127.2, 127.0 (d, J=5.5 Hz), 126.7, 125.5, 124.3, 120.4, 120.3, 120.1, 111.9, 106.7, 60.6 (d, J=3.2 Hz), 44.0, 37.7 (d, J=3.3 Hz), 34.9, 33.6, 33.4, 30.3, 30.1, 29.9, 16.2. HRMS (ESI) calcd for $C_{52}H_{65}N_2P[M+H]^+$: 749.4958. Found: 749.4959.

Example 10

Synthesis of (R)- N-(4-t-butylpyridyl-2-methyl)-7-di-(3,5-di-tert-butylphenyl) phosphino-7'-amino-1,1'-spiro-dihydro-indene (Ij)

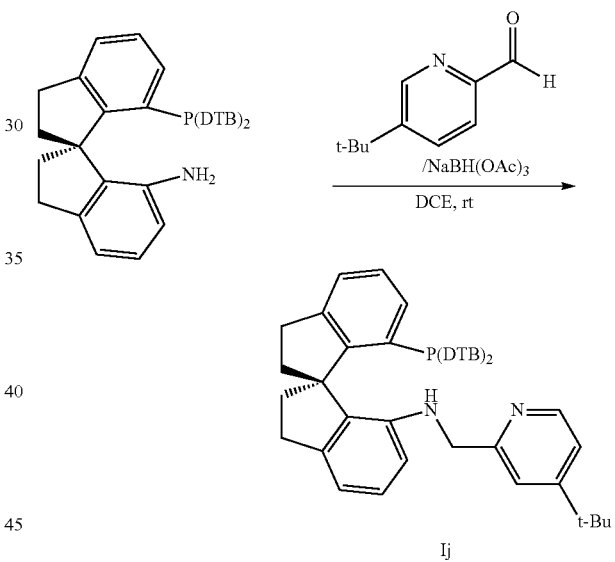

Specific process can be found in Example 1, and white solid was obtained with a yield of 95%.

Mp 86-88° C., $[\alpha]_D^{20}$ +204 (c 1.0, $CH_2Cl_2$), $^1H$ NMR (400 mhz, $cdcl_3$) δ 8.14 (d, J=5.2 Hz, 1H), 7.32 (d, J=7.6 Hz, 1H), 7.22-7.18 (m, 3H), 7.12-7.08 (m, 2H), 6.99 (d, J=5.2 Hz, 1H), 6.93 (brs, 1H), 6.82 (d, J=8 Hz, 2H), 6.73 (d, J=7.6 Hz, 2H), 6.69 (d, J=7.2 Hz, 1H), 6.15 (d, J=7.6 Hz, 1H), 4.40-4.39 (m, 1H), 4.03-3.97 (m, 1H), 3.54-3.58 (m, 1H), 3.14-2.91 (m, 3H), 2.86-2.80 (m, 1H), 2.52-2.44 (m, 1H), 2.20-2.09 (m, 3H), 1.19 (s, 9H), 1.15 (s, 18H), 1.05 (s, 18H); $^{31}P$ NMR (162 mhz, $cdcl_3$) δ −18.55 (s); $^{13}C$ NMR (100 mhz, $cdcl_3$) δ 158.8, 156.9, 151.7, 151.4, 148.7 (d, J=6.2 Hz), 147.5, 143.1, 143.0, 142.9 (d, J=11.8 Hz), 134.0 (d, J=12.4 Hz), 133.7, 133.5, 132.8, 131.8 (d, J=3.5 Hz), 127.2, 127.0 (d, J=5.4 Hz), 126.8 (d, J=4.4 Hz), 125.8, 124.7, 121.0, 120.2, 117.6, 116.6, 127.7, 107.6, 60.6 (d, J=3.3 Hz), 47.1, 37.7 (d, J=3.6 Hz), 34.7, 33.7, 33.6, 33.5, 30.3, 30.2, 29.8, 29.4. HRMS (ESI) calcd for $C_{55}H_{71}N_2P[M+H]^+$: 791.5428. Found: 791.5430.

Example 11

Application of Chiral Spiro-Pyridylamidophosphine Ligand (R)-Ii (Prepared in Example 9) in the Asymmetric Catalytic Hydrogenation Reaction of Carbonyl Compounds

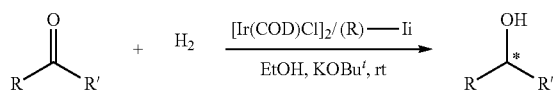

Under the protection of nitrogen atmosphere, 0.5 mg (0.74 gmol) [Ir(COD)Cl]$_2$, 1.2 mg (1.6 μmol) (R)-Ii were added to the inner hydrogenation tube. Subsequently, 1 ml absolute ethyl alcohol was added and stirred for 1 h at room temperature. The inner reaction tube was placed into the hydrogenation reactor. After substitution by hydrogen, the reaction was stirred for 1 h at a hydrogen pressure of 1 atmosphere. The reactor was opened, and 7.5-150 mmol substrate (solid substrate, added after dissolved by ethanol) was added, followed by 0.05-25 mmol potassium tert-butoxide solution in ethanol (0.5 ml (0.1 mmol/mL)-25 ml (1 mmol/mL)) added with a syringe. The reactor was sealed, and hydrogen was filled to a pressure of 8-10 atm, and the reaction was stirred under the hydrogen pressure at room temperature for a while ranging from 10 minutes to 24 hours. After the hydrogenation was finished, the reaction solution was filtered through a short silica gel column to remove the catalyst, and the conversion rate and yield of the reaction were analyzed by gas chromatography or nuclear magnetic resonance (NMR); and the optical purity of the product was analyzed by gas chromatography or high performance liquid chromatography. The results of the hydrogenation experiments were listed in Table 1.

TABLE 1

| No. | Carbonyl Compound | S/C | reaction duration | yield (%) | Ee (%) |
|---|---|---|---|---|---|
| 1 |  | 5000 | 20 min | 100 | 98 |
| 2 |  | 100,000 | 18 h | 100 | 98 |
| 3 |  | 1,000,000 | 31 h | 100 | 98 |
| 4 |  | 5000 | 40 min | 98 | 96 |
| 5 |  | 5000 | 40 min | 97 | 97 |
| 6 |  | 5000 | 50 min | 98 | 98 |

TABLE 1-continued

Asymmetric catalytic hydrogenation of carbonyl compounds

| No. | Carbonyl Compound | S/C | reaction duration | yield (%) | Ee (%) |
|---|---|---|---|---|---|
| 7 | 3-bromoacetophenone | 5000 | 50 min | 98 | 98 |
| 8 | 3-methoxyacetophenone | 5000 | 50 min | 100 | 98 |
| 9 | 2-methoxyacetophenone | 5000 | 40 min | 100 | 99.8 |
| 10 | 2-chloroacetophenone | 5000 | 35 min | 97 | 99 |
| 11 | 3,5-bis(trifluoromethyl)acetophenone | 5000 | 1.5 h | 98 | 99 |
| 12[a] | methyl 2-pentanoylbenzoate | 1000 | 1 h | 98 | 98 |
| 13 | 1-tetralone | 5000 | 30 min | 99 | 78 |
| 14 | 1-indanone | 5000 | 1.5 h | 94 | 72 |
| 15 | phenylacetone | 1000 | 3 h | 100 | 25 |

TABLE 1-continued

Asymmetric catalytic hydrogenation of carbonyl compounds

| No. | Carbonyl Compound | S/C | reaction duration | yield (%) | Ee (%) |
|---|---|---|---|---|---|
| 16 | 1-cyclohexylethan-1-one | 1000 | 10 min | 100 | 88 |
| 17 | ethyl 3-oxo-3-phenylpropanoate | 1000 | 1 h | 98 | 98 |
| 18 | ethyl 3-oxo-3-phenylpropanoate | 100,000 | 19 h | 97 | 99 |
| 19 | ethyl 3-oxo-3-(p-tolyl)propanoate | 1000 | 25 min | 97 | 99 |
| 20 | ethyl 3-(4-chlorophenyl)-3-oxopropanoate | 1000 | 1 h | 94 | 96 |
| 21 | ethyl 3-(3-bromophenyl)-3-oxopropanoate | 1000 | 1.5 h | 95 | 95 |
| 22 | ethyl 3-(3-methoxyphenyl)-3-oxopropanoate | 1000 | 1.5 h | 93 | 96 |
| 23 | ethyl 3-(2-chlorophenyl)-3-oxopropanoate | 1000 | 4 h | 97 | 99 |
| 24 | ethyl 3-(2-methoxyphenyl)-3-oxopropanoate | 1000 | 50 min | 94 | 99.5 |
| 25 | ethyl acetoacetate | 1000 | 30 min | 100 | 50 |

TABLE 1-continued

Asymmetric catalytic hydrogenation of carbonyl compounds

| No. | Carbonyl Compound | S/C | reaction duration | yield (%) | Ee (%) |
|---|---|---|---|---|---|
| 26 | | 100 | 2 h | 80 | 88 |
| 27 | | 1,000 | 4 h | 79 | 0 |
| 28[b] | | 1000 | 25 min | 98 | 92 |
| 29 | | 1000 | 20 min | 95 | 98 |
| 30 | | 1000 | 40 h | 85 | 100 |

Note:
[a] the product has the structure of lactone formed by transesterification after hydrogenation;
[b] the reaction was carried out at 0° C.

The chiral spiro-pyridylamidophosphine ligand compound provided herein, the synthesis method and its application have been described by examples, and it is apparent that modification, or appropriate change and combination can be made to the chiral spiro-pyridylamidophosphine ligand compounds described herein, the synthesis method and its application by those skilled in the art, without departing from the contents, spirit and scope of the present invention, in order to achieve the present invention. In particular, it should be pointed out that all similar replacements and modifications become apparent to those skilled in the art, and they are deemed to be within the spirit, scope and contents of the present invention.

The invention claimed is:

1. Chiral spiro-pyridylamidophosphine compound having the structure of Formula (I), or a racemate or optical isomer thereof, or a catalytically acceptable salt thereof,

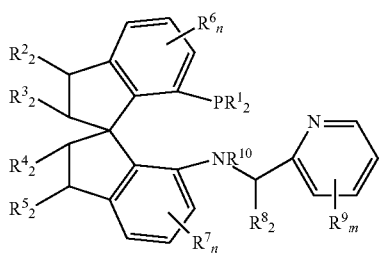

I wherein, $R^1$ is $C_1$-$C_8$ chain hydrocarbyl or saturated cyclic hydrocarbyl or cycloalkenyl, phenyl, substituted phenyl, 1-naphthyl, 2-naphthyl, heteroaryl, furyl or thienyl, and the substituent on said substituted phenyl is halogen, $C_1$-$C_8$ hydrocarbyl or alkoxy, with a substituent amount of 1-5, and said heteroaryl is pyridyl;

$R^2$, $R^3$, $R^4$ and $R^5$ are H, $C_1$-$C_8$ alkyl or alkoxy, phenyl, substituted phenyl, 1-naphthyl, 2-naphthyl, heteroaryl, furyl or thienyl, and the substituent on said substituted phenyl is $C_1$-$C_8$ alkyl or alkoxy, with a substituent amount of 1-5, and said heteroaryl is pyridyl; or $R^2$ and $R^3$, $R^4$ and $R^5$ are incorporated into $C_3$-$C_7$ aliphatic ring or aromatic ring, respectively; $R^2$, $R^3$, $R^4$ and $R^5$ can be the same or different;

$R^6$, $R^7$ are H, $C_1$-$C_8$ alkyl, $C_1$-$C_8$ alkoxy, $C_1$-$C_8$ aliphatic amido group, and n=0-3; or when n≥2, two adjacent $R^6$ groups or two adjacent $R^7$ groups can be incorporated into $C_3$-$C_7$ aliphatic ring or aromatic ring, and $R^6$, $R^7$ can be the same or different;

$R^8$, $R^9$ are H, halogen, $C_1$-$C_8$ alkyl, $C_1$-$C_8$ alkoxy, phenyl, substituted phenyl, 1-naphthyl, 2-naphthyl, heteroaryl, furyl or thienyl, and the substituent on said substituted phenyl is halogen, $C_1$-$C_8$ alkyl or alkoxy, with a substituent amount of 1-5, and said heteroaryl is pyridyl, and m=0-3; or when m≥2, adjacent $R^9$ or $R^8$ and $R^9$ groups can be incorporated into $C_3$-$C_7$ aliphatic ring or aromatic ring, and $R^8$, $R^9$ can be the same or different;

$R^{10}$ is H, $C_1$-$C_8$ alkyl, phenyl, substituted phenyl, 1-naphthyl, 2-naphthyl, heteroaryl, furyl or thienyl, and the substituent on said substituted phenyl is $C_1$-$C_8$ hydrocarbyl or alkoxy, with a substituent amount of 1-5, and said heteroaryl is pyridyl.

2. The chiral spiro-pyridylamidophosphine compound according to claim 1, or the racemate or optical isomer thereof, or the catalytically acceptable salt thereof, which is characterized by that in the structural formula of said compound, $R^2$, $R^3$, $R^4$, $R^5$, $R^6$, $R^7$, $R^8$, $R^{10}$ are H simultaneously, and $R^1$ is phenyl or substituted phenyl, and the substituent on said substituted phenyl is halogen, $C_1$-$C_8$ alkyl or alkoxy, with a substituent amount of 1-5; $R^9$ is H, halogen, $C_1$-$C_8$ alkyl, $C_1$-$C_8$ alkoxy, phenyl, substituted phenyl, 1-naphthyl, 2-naphthyl, heteroaryl, furyl or thienyl, and the substituent on said substituted phenyl is halogen, $C_1$-$C_8$ hydrocarbyl or alkoxy, with a substituent amount of 1-5, and said heteroaryl is pyridyl, and m=0-3; or when m≥2, adjacent $R^9$ groups can be incorporated into $C_3$-$C_7$ aliphatic ring or aromatic ring.

3. The chiral spiro-pyridylamidophosphine compound according to claim 1, or the racemate or optical isomer thereof, or the catalytically acceptable salt thereof, which is characterized by that the structural formulae of said compounds are as follows:

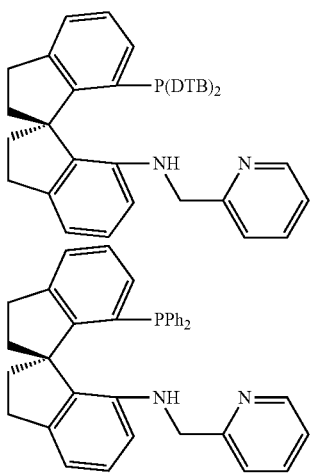

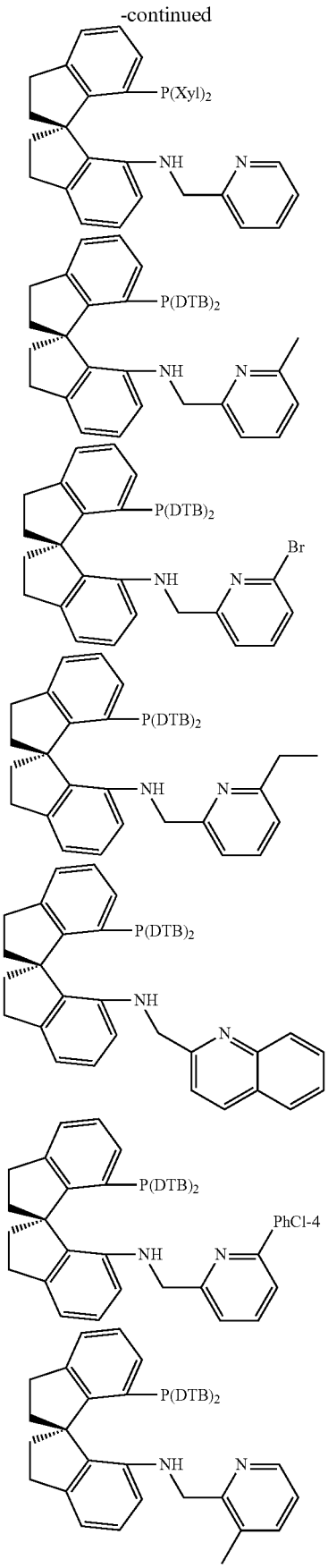

-continued

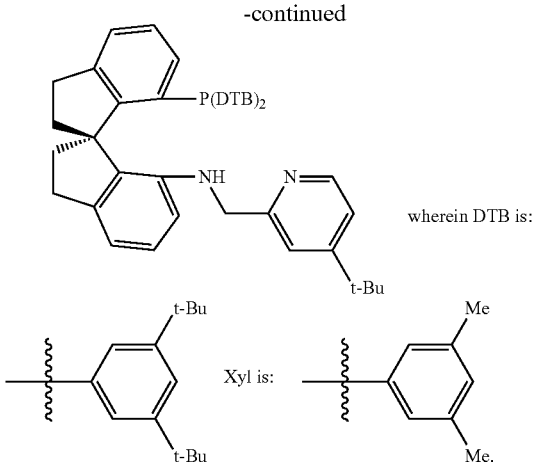

wherein DTB is: [structure with t-Bu groups]

Xyl is: [structure with Me groups]

4. A method for synthesizing the chiral spiro-pyridylamidophosphine compound according to claim 1, which is characterized by that, preparation is performed via the following reactions using the racemically or optically active compound of Formula (II) as the starting material:

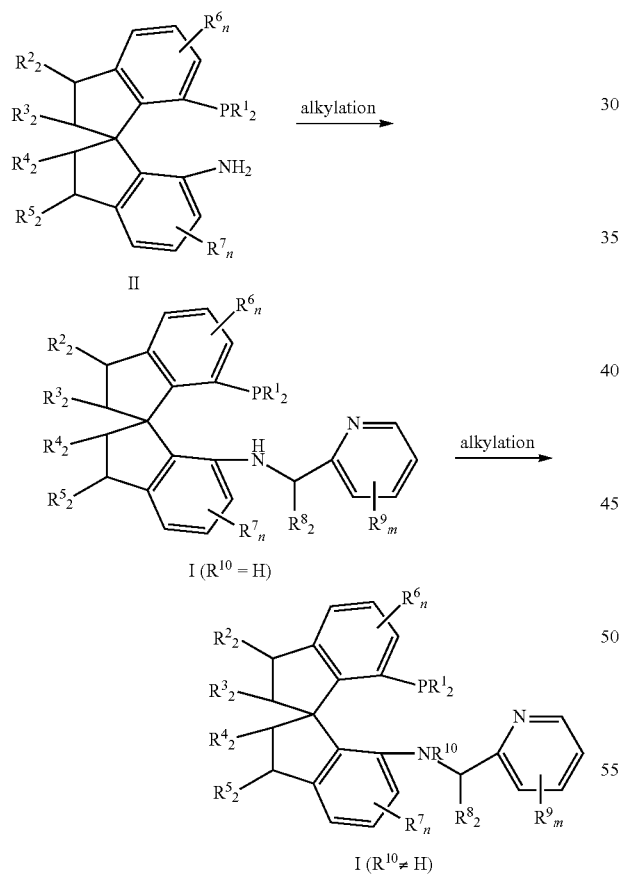

wherein, $R^1$-$R^{10}$ and values of n and m are defined as claim 1.

5. The synthesis method according to claim 4, which is characterized by the following steps:

Step 1:
racemically or optically active compound having the structure of Formula (II) is reacted with substituted pyridylaldehyde or pyridone in a reactor for 2-24 hours in the presence of organic solvent and reducing agent to obtain spiro-pyridylamidophosphine compound I with one hydrogen atom contained on corresponding nitrogen atom ($R^{10}$=H); the molar ratio among said racemically or optically active compound of Formula (II), pyridylaldehyde or pyridone, and reducing agent is in the range of 1:1~5:1~10; and the reaction temperature is 0-120° C.; or racemically or optically active compound having the structure of Formula (II) is initially reacted with pyridine formyl chloride in a reactor in the presence of organic solvent and alkali to obtain a corresponding acylated compound, which is then reduced by a reducing agent to obtain the spiro-pyridylamidophosphine compound I with one hydrogen atom contained on corresponding nitrogen atom ($R^{10}$=H); wherein in the acylation reaction, the molar ratio among said racemically or optically active compound of Formula (II), pyridine formyl chloride and the alkali is in the range of 1:1~5:1~10, and the reaction temperature is 0~100° C.; wherein in the reduction reaction, the molar ratio of the acylated compound to the reducing agent is in the range of 1:1~10 and the reaction temperature is from −20 to 100° C.; or racemically or optically active compound having the structure of Formula (II) is initially reacted with pyridine formic acid via acylation reaction in a reactor in the presence of organic solvent, alkali and carboxyl-activating reagent to obtain a corresponding acylated compound, which is then reduced by a reducing agent to obtain the spiro-pyridylamidophosphine compound I with one hydrogen atom contained on corresponding nitrogen atom ($R^{10}$=H); wherein in the acylation reaction, the molar ratio among said racemically or optically active compound of Formula (II), pyridine formic acid and the activating reagent is in the range of 1:1~5:1~10, and the reaction temperature is from −30 to 100° C.; wherein in the reduction reaction, the molar ratio of the resulting acylated compound to the reducing agent is in the range of 1:1~10, and the reaction temperature is from −20 to 100° C.;

step 2:
according to the method or procedure in step 1, the spiro-pyridylamidophosphine compound I with no hydrogen atom attached to the nitrogen atom ($R^{10}$≠H) is synthesized by replacing the pyridylaldehyde, pyridine formyl chloride, pyridine formic acid described above with fatty aldehyde or aromatic aldehyde, acyl chloride, carboxylic acid, respectively, and using the synthesized compound I ($R^{10}$=H) as the starting material, in the above synthesis method, the molecular formula of said substituted pyridylaldehyde, pyridone, pyridine formyl chloride, pyridine formic acid and the fatty aldehyde or the aromatic aldehyde, acyl chloride, carboxylic acid are defined by $R^8$~$R^{10}$ and the values of m according to claim 1.

6. The synthesis method according to claim 5, which is characterized by that, said organic solvent may be any one of methanol, ethanol, propanol, isopropanol, butanol, tetrahydrofuran, toluene, xylene, methyl tert-butyl ether, diethyl ether, dioxane, N,N-dimethyl formamide, dimethyl sulfoxide, or any mixture thereof.

7. The synthesis method according to claim 5, which is characterized by that, said reducing agent may be lithium aluminium hydride, sodium borohydride, sodium triacetyl borohydride or sodium cyanoborohydride.

8. The synthesis method according to claim 5, which is characterized by that, said alkali is an organic base or an inorganic base, wherein said organic base may be pyridine, triethylamine, tributyl amine, N-methylmorpholine or N,N-diethyl isopropyl amine; said inorganic base may be sodium hydroxide, potassium hydroxide, sodium carbonate or potassium carbonate; and said carboxyl-activating reagent is ethyl chloroformate, isopropyl chloroformate, N,N'-dicyclohexyl-carbodiimide or carbonyl diimidazole.

9. A chiral catalyst,
which was obtained by the complexation reaction of the chiral spiro-pyridylamidophosphine compound according to claim 1 and iridium catalyst precursor in the organic solvent; followed by 0.1-3 hours of reaction stirred under the hydrogen atmosphere at the pressure of 0.1-10 Mpa; or
which was obtained by desolventization of the reaction solution after the complexation reaction to obtain the complex, which is then redissolved in the organic solvent, stirred under the hydrogen atmosphere at the pressure of 0.1-10 Mpa for 0.1-3 hours.

10. The chiral catalyst according to claim 9, which is characterized by that, said iridium catalyst precursor is [Ir(cod)]$Cl_2$ (cod=cyclooctadiene), [Ir(cod)$_2$]$BF_4$, [Ir(cod)$_2$]$PF_6$, [Ir(cod)$_2$]$SbF_6$ or [Ir(cod)$_2$]OTf.

11. The chiral catalyst according to claim 9, which is characterized by that, the organic solvent is one of methanol, ethanol, propanol, isopropanol, butanol, tetrahydrofuran, toluene, methyl tert-butyl ether, dioxane, DMF, DMSO, or any mixture thereof.

12. A method for preparing a chiral alcohol compound, which is characterized by that, in the organic solvent, a carbonyl compound and an alkali are added into a reaction solution comprising the chiral catalyst according to claim 9, and are reacted by stirring under the hydrogen atmosphere at the pressure of 0.1-10 Mpa for 0.1-24 hours to obtain the chiral alcohol compound.

13. The method according to claim 12, which is characterized by that, said carbonyl compound is aryl alkyl ketone, ketene or keto ester.

14. The method according to claim 12, which is characterized by that, the organic solvent is any one of methanol, ethanol, propanol, isopropanol, butanol, tetrahydrofuran, toluene, methyl tert-butyl ether, dioxane, DMF, DMSO, or any mixture thereof.

15. The method according to claim 12, which is characterized by that, said alkali is sodium hydroxide, potassium hydroxide, sodium carbonate, potassium carbonate, sodium ethoxide, potassium ethoxide, sodium tert-butoxide, potassium tert-butoxide, lithium tert-butoxide, triethyl amine, tributyl amine or N-methyl morpholine.

16. A method for preparing a chiral alcohol compound, which is characterized by the following steps:
1) hydrogenated chiral catalyst was obtained by the initial 0.5-4 hours of complexation reaction of the chiral spiro-pyridylamidophosphine compound according to claim 1 and iridium catalyst precursor in an organic solvent at 25-120° C., followed by 0.1-3 hours of reaction stirred under the hydrogen atmosphere at the pressure of 0.1-10 Mpa; or
complexation reaction between chiral spiro-pyridylamidophosphine compound and iridium catalyst precursor is performed in an organic solvent for 0.5-4 hours, then desolventization is performed to obtain the corresponding complex, which is then subjected to reaction under stirring in the organic solvent under the hydrogen atmosphere at the pressure of 0.1-10 Mpa for 0.1-3 hours, to obtain the chiral catalyst;
2) in an organic solvent, the resulting reaction solution or solid mentioned above is reacted as catalyst with a carbonyl compound and an alkali added by stirring under the hydrogen atmosphere at the pressure of 0.1-10 Mpa for 0.1-24 hours to obtain the chiral alcohol compounds.

17. The method according to claim 16, which is characterized by that, said iridium catalyst precursor is [Ir(cod)]$Cl_2$ (cod=cyclooctadiene), [Ir(cod)$_2$]$BF_4$, [Ir(cod)$_2$]$PF_6$, [Ir(cod)$_2$]$SbF_6$ or [Ir(cod)$_2$]OTf.

18. The method according to claim 16, which is characterized by that, said carbonyl compound is aryl alkyl ketone, ketene or keto ester.

19. The method according to claim 16, which is characterized by that, said alkali is sodium hydroxide, potassium hydroxide, sodium carbonate, potassium carbonate, sodium ethoxide, potassium ethoxide, sodium tert-butoxide, potassium tert-butoxide, lithium tert-butoxide, triethyl amine, tributyl amine or N-methyl morpholine.

20. The method according to claim 16, which is characterized by that, the organic solvent as described in step 1) and 2) is any one of methanol, ethanol, propanol, isopropanol, butanol, tetrahydrofuran, toluene, methyl tert-butyl ether, dioxane, DMF, DMSO, or any mixture thereof.

* * * * *